United States Patent
Tziviskos et al.

(10) Patent No.: US 8,027,735 B1
(45) Date of Patent: Sep. 27, 2011

(54) ATRAUMATIC HIGH-RETENTION HEADPIECE

(75) Inventors: George Tziviskos, Encino, CA (US); Michael D. Brownen, Keller, TX (US); William G. Orinski, Stevenson Ranch, CA (US)

(73) Assignee: Advanced Bionics, LLC, Valencia, CA (US)

( * ) Notice: Subject to any disclaimer, the term of this patent is extended or adjusted under 35 U.S.C. 154(b) by 239 days.

(21) Appl. No.: 12/415,977

(22) Filed: Mar. 31, 2009

Related U.S. Application Data

(60) Provisional application No. 61/041,338, filed on Apr. 1, 2008.

(51) Int. Cl.
*A61N 1/00* (2006.01)

(52) U.S. Cl. .......................................... 607/57

(58) Field of Classification Search .............. 607/57, 607/61, 88; 600/16, 485
See application file for complete search history.

(56) References Cited

U.S. PATENT DOCUMENTS

| | | | |
|---|---|---|---|
| 4,082,097 A | 4/1978 | Mann et al. | |
| 4,352,960 A | 10/1982 | Dormer et al. | |
| 4,726,378 A | 2/1988 | Kaplan | |
| 5,214,404 A | 5/1993 | Yamaguchi et al. | |
| 5,312,439 A | 5/1994 | Loeb | |
| 5,324,316 A | 6/1994 | Schulman et al. | |
| 5,358,514 A | 10/1994 | Schulman et al. | |
| 5,545,191 A | 8/1996 | Mann et al. | |
| 5,603,726 A | 2/1997 | Schulman et al. | |
| 5,613,935 A * | 3/1997 | Jarvik .............................. | 600/16 |
| 5,621,369 A | 4/1997 | Gardner et al. | |
| 5,948,006 A | 9/1999 | Mann | |
| 6,048,601 A | 4/2000 | Yahagi et al. | |
| 6,275,737 B1 | 8/2001 | Mann | |
| 6,324,430 B1 | 11/2001 | Zarinetchi et al. | |
| 6,372,323 B1 | 4/2002 | Kobe et al. | |
| 6,610,382 B1 | 8/2003 | Kobe et al. | |
| 6,904,615 B2 | 6/2005 | Kobe et al. | |
| D512,416 S | 12/2005 | Medina Malaver | |

(Continued)

FOREIGN PATENT DOCUMENTS

WO 0020210 A1 4/2000

(Continued)

OTHER PUBLICATIONS

Retainer Discs retrieved from http://www.cochlearstore.com/index.php?main_page=product_info&cPath=1_11&products_id=68 on Mar. 23, 2009..

(Continued)

*Primary Examiner* — George Manuel
*Assistant Examiner* — Robert Wieland
(74) *Attorney, Agent, or Firm* — Henricks, Slavin & Holmes LLP

(57) ABSTRACT

A headpiece for a cochlear implant system includes a transcutaneous transmission coil that transfers power and/or data to an implantable device implanted under a user's skin. The headpiece includes a magnet for holding the transmission coil in close proximity to the receiver coil in the implanted device, which also contains a magnet, and provides the desired alignment between the coils so that inductive coupling may efficiently occur. The headpiece has a bottom surface for skin contact that includes a plurality of flexible bumps configured to distribute pressure over a large surface area while allowing blood flow throughout the area. This also provides friction contact with the skin to help secure the headpiece, reducing movement due to lateral loading, while reducing skin irritation and erosion.

25 Claims, 8 Drawing Sheets

U.S. PATENT DOCUMENTS

| | | |
|---|---|---|
| 7,225,032 B2 | 5/2007 | Schmeling et al. |
| 7,286,880 B2 | 10/2007 | Olson et al. |
| 7,286,881 B2 | 10/2007 | Schommer et al. |
| 7,309,519 B2 | 12/2007 | Scholz et al. |
| 7,340,310 B2 | 3/2008 | Nitzan et al. |
| 7,729,774 B1 | 6/2010 | Lynch et al. |
| 2002/0087204 A1* | 7/2002 | Kung et al. ............ 607/61 |
| 2006/0030905 A1* | 2/2006 | Medina Malaver ............ 607/61 |
| 2006/0184051 A1* | 8/2006 | Hempstead et al. ............ 600/485 |
| 2007/0030442 A1* | 2/2007 | Howell et al. ............ 351/158 |
| 2007/0055321 A1 | 3/2007 | Gordon et al. |
| 2009/0143839 A1 | 6/2009 | Zimmerling |

FOREIGN PATENT DOCUMENTS

| | | |
|---|---|---|
| WO | 0213638 A3 | 2/2002 |
| WO | 0213638 A2 | 1/2003 |
| WO | 2007130176 A1 | 11/2007 |
| WO | 2010083554 A1 | 7/2010 |

OTHER PUBLICATIONS

Antenna coil having a ring of plastic bumps.

FDA.pdf retrieved from http://www.accessdata.fda.gov/scripts/cdrh/cfdocs/cfPMA/PMA.cfm?ID=16034 on Jan. 20, 2009.

Platinum Series(tm) headpiece.

\* cited by examiner

Fig. 1C  Fig. 1D

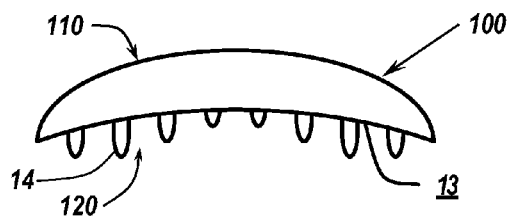
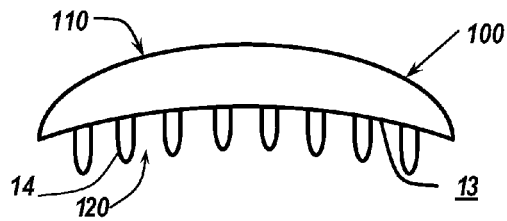
Fig. 2          Fig. 2A
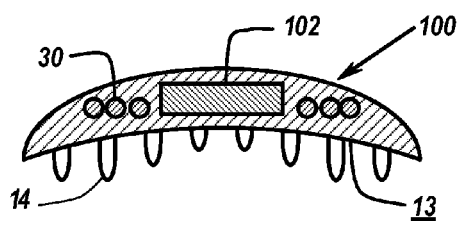
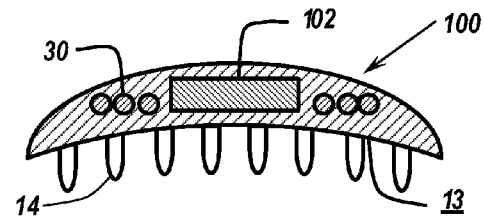
Fig. 3          Fig. 3A
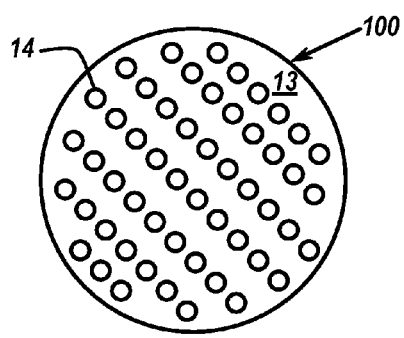
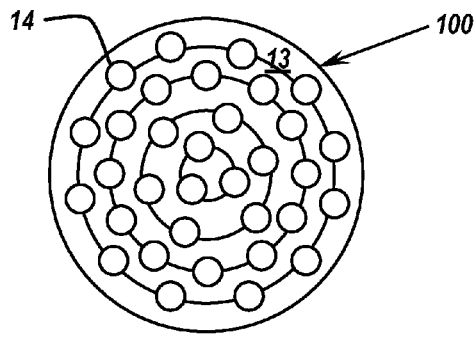
Fig. 4          Fig. 4A

US 8,027,735 B1

ATRAUMATIC HIGH-RETENTION HEADPIECE

RELATED APPLICATIONS

The present application claims the benefit under 35 U.S.C. §119(e) to U.S. Provisional Patent Application No. 61/041,338, filed on Apr. 1, 2008, which is herein incorporated by reference in its entirety.

BACKGROUND OF INVENTION

The present invention relates to the transfer of electromagnetic energy between coils, and more particularly, to an external device secured to the skin of a patient, having a coil for transmitting power and/or data to an implanted device and/or to a replenishable power source associated with the implanted device.

The present invention will be described in the context of a cochlear implant system; however, it should be understood that it is also useful for other medical devices such as neuromuscular stimulators, implantable pumps, and other implantable devices that are designed to be surgically inserted within a patient's body to carry out a medically related function for an extended period of time. Indeed, the present invention can be used in any device having an implantable portion including an implanted coil and an external portion containing an external coil for placement on the skin of the patient in alignment with the implanted coil. In a cochlear implant system, the portion of the system containing the external coil is placed on the head and is referred to as the "headpiece". The term "headpiece" will be used herein to refer to the portion of the system containing the external coil, regardless of where it is used on the body.

A common way of achieving alignment between an external coil and an implanted coil is to employ a magnet in both the headpiece and the implanted device. The magnetic attractive force associated with such magnets holds the external coil in close proximity to the implanted coil and provides the desired alignment between the coils for efficient electromagnetic coupling, which may be RF, inductance, optical, or the like.

However, a known problem is that the pressure of the headpiece against the skin may cause skin irritation and/or tissue damage due to blood flow restriction. The issue is further compounded by variable skin curvatures resulting, in part, from the shape of the implanted device and variable skin thicknesses among patients. Because of this, force may be applied over a small area of the skin flap, resulting in very high local pressures, which can lead to irritation, soreness, redness, and even necrosis of the skin flap tissue or extrusion of the implanted device. Reducing magnetic forces to address the pressure issues has the undesirable effect of poor headpiece retention.

Attempts have been made to improve headpiece comfort and retention by providing a textured elastomeric material at the periphery on the skin side surface of the headpiece, or providing a ring or disk of textured rubber having adhesive on one side to stick to the skin side surface of the headpiece. U.S. patent application Ser. No. 10/741,411, filed Dec. 19, 2003, which is incorporated herein by reference, discloses a shell for covering a headpiece in which portions of the shell that come into contact with skin are covered with or made of a material that is comfortable against the skin; a material such as fabric or foam or other material with similar qualities may be used to maintain a comfortable feel against the skin in moist environments, such as when a user sweats. Other headpiece designs have used an open antenna coil design having a ring of rigid plastic bumps at the perimeter on the skin side surface.

In view of the above, what is needed is a headpiece that can transmit power and/or data transcutaneously to an implanted device, wherein such headpiece is readily attachable to the skin in close proximity to the implanted device, easily and reliably retained in proper alignment with the implanted device, and does not promote skin erosion, irritation, or discomfort, even with minor changes of the skin that commonly occur.

SUMMARY OF INVENTION

The present invention solves the above and other needs by providing a magnet- and coil-containing headpiece with bottom surface having a plurality of flexible bumps that define multiple low- and zero-pressure channels. This allows blood to flow in nearly every part of the skin and tissue underneath the headpiece. Because the bumps can resiliently deform and flex independently, the headpiece conforms to the contour of the skin, thus more evenly distributing headpiece forces over a larger skin area, further improving comfort and blood flow. Additionally, the resiliency of the bumps allows for the headpiece to dynamically conform to the skin with minor changes of the skin. Such changes can occur as the surgical wound heals, with swelling that can last one or two months following surgery. Changes to skin flap thickness can also occur with pregnancy, water retention, weight gain or loss, age, hair growth, and movement with chewing or talking. This ability to conform to the contour of the skin allows the headpiece to adjust naturally to small changes, being relatively insensitive to magnet strength, such that the magnet strength does not need to be adjusted as often by adding, subtracting, or replacing magnets in the headpiece. While major changes may require such adjustment, minor changes will be accommodated by the flexible bumps.

The bump configuration, shape, surface finish, and material can be used to provide a high-friction interface to reduce movement of the headpiece under lateral loading, thereby improving retention of the headpiece.

In some embodiments of the invention, a rigid bottom surface may be used to provide support for the bumps, allowing use of the softest possible materials for the bumps themselves, further improving comfort and reducing pressure without compromising retention.

BRIEF DESCRIPTION OF ACCOMPANYING DRAWINGS

The above and other aspects, features and advantages of the present invention will be more apparent from the following more particular description thereof, presented in conjunction with the following drawings wherein:

FIGS. 1A-1E are perspective and side views, of an embodiment of the present invention;

FIGS. 2 and 2A are side views of two embodiments of the present invention;

FIGS. 3 and 3A are side cross sectional views of two embodiments of the present invention;

FIGS. 4 and 4A are bottom (skin-side) views of two embodiments of the present invention;

Corresponding reference characters indicate corresponding components throughout the several views of the drawings.

DETAILED DESCRIPTION OF INVENTION

The following description of the presently contemplated best mode of practicing the invention is not to be taken in a limiting sense, but is made merely for the purpose of describing the general principles of the invention. The scope of the invention should be determined with reference to the claims.

Figure 1:
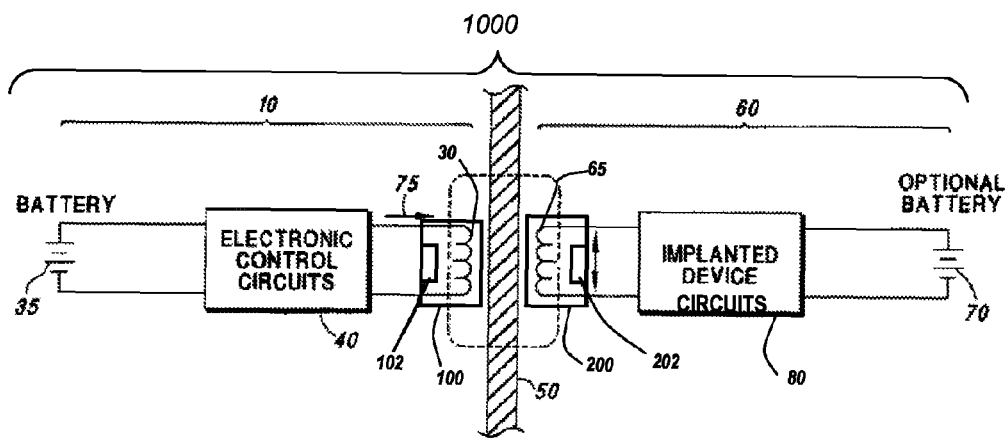
FIG. 1 is a block/schematic view.
Figure 1A:
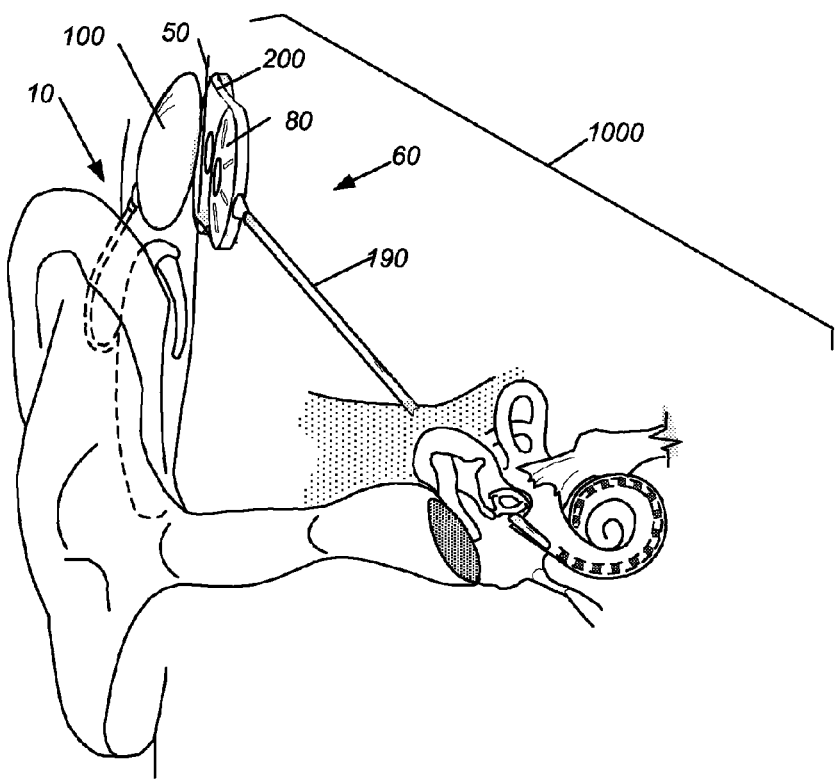

Referring first to FIGS. 1 and 1A, there are shown a schematic diagram and perspective illustration of a cochlear implant system 1000 having external componentry 10 and implanted componentry 60. The implanted componentry 60 may comprise a single implanted device or may comprise two or more separate devices that can be detachably attached to each other; for example, a lead may be permanently integrated with an implantable cochlear stimulator (ICS), or a battery may be sealed within the housing of the ICS, or the lead and/or battery may be detachably attachable to the ICS, or the ICS may otherwise be modular. As used herein, the terms "implanted device" and "cochlear implant" refer to the implanted componentry, whether it is a single device or separate devices working together as part of the implanted portion of the system. Implanted device 60 comprises a coil 65 and a magnet 202 positioned in a portion 200 of implanted device 60 such that when implanted, coil 65 and magnet 202 are located proximate the skin 50.

Just as the implanted componentry may comprise a single implanted device or multiple components, external componentry 10 may comprise a single integrated device, such as described in U.S. patent application Ser. No. 12/398,058 entitled "Integrated Cochlear Implant Headpiece," or a modular device, such as described in U.S. patent application Ser. No. 12/397,982 entitled "Modular Speech Processor Headpiece," which are incorporated herein by reference in their entirety. Alternatively, external componentry 10 may comprise separate external components that work together and can be individually selected and individually replaced, such as the battery 35 of the behind the ear processor shown in FIG. 1B. External componentry 10 comprises headpiece 100, which includes a coil 30 for transmitting power and/or data through the skin 50 to implanted device 60 via an RF or other electromagnetic link that couples power from external coil 30 to internal coil 65. So long as a suitable link, e.g., an inductive link, is established between these two coils, power and/or data can be continuously supplied to the implanted device 60 from the external device 10.

The efficiency with which electromagnetic power may be transcutaneously transferred between a transmission coil and a receiving coil is a function of the alignment and distance between the coils. It is thus desirable to position the external device 10 as close as possible to the implanted device 60. In use, headpiece 100 is located as close as possible to implanted device 60 so as to provide the strongest signal coupling between coils 30 and 65. Headpiece 100 includes a magnet 102 to magnetically couple to internal magnet 202 of implanted device 60 to retain headpiece 100 against the skin. The magnetic attractive force holds external coil 30 in close proximity to internal coil 65 and provides the desired alignment between the coils so that inductive coupling may efficiently occur. Either or both of magnets 102 and 202 may be fixed or detachable. For example, it may be advantageous to be able to temporarily take away the internal magnet 202 in order to use magnetic resonance imaging (MRI). It also may be advantageous to be able to take out external magnet 102 to install one or more magnets of various strengths in headpiece 100.

Optionally, headpiece 100 may be constructed of flexible non-rigid materials in order to conform to the contour of the portion of the user's skin 50 to which the headpiece 100 is attached and can be made in a variety of shapes and colors, such as various skin tones or designer colors or patterns. The headpiece is preferably thin and lightweight.

In addition to external coil 30 and magnet 102, external componentry 10 includes a power source 35 and control circuitry 40. The power source 35 and control circuitry 40 may be located on a person's belt or pocket or behind the ear (BTE), and attached to external coil 30 via a cable. See, e.g., U.S. Pat. No. 5,603,726, which is incorporated herein by reference. Alternatively, power source 35 and/or control circuitry 40 may be included within headpiece 100 housing coil 30. See, e.g., U.S. Pat. No. 5,948,006 and U.S. patent application Ser. Nos. 12/398,058 and 12/397,982, which are incorporated herein by reference. In either case, most or all of electronic circuitry 40 may be embodied in one or more integrated circuits (IC).

Headpiece 100 transmits a modulated signal 75 from external transmission coil 30, through skin 50, to internal receiving coil 65 of implanted device 60. Modulated signal 75 is controlled by electronic circuitry 40 powered by a battery or other power source 35 (e.g., a supercapacitor, ultracapacitor, or other energy-storage device). Circuitry 80 within implanted device 60 demodulates the signal to obtain data, and/or rectifies the signal to obtain power, as is known in the art. The recovered data may be used to control the operation of implanted device 60. Hence, headpiece 100 is able to selectively control and/or power implanted device 60.

Some implantable devices, such as neural or auditory stimulators, do not require internal batteries as a power source, but rather receive power directly via transcutaneous coupling. See, e.g., U.S. Pat. No. 5,603,726, which describes an implantable cochlear stimulator powered by an external wearable system and is incorporated herein by reference.

Other implantable devices contain an optional battery or other power source 70, e.g., an ultracapacitor. The optional power source 70 is preferably of the secondary type, which can be recharged by transcutaneously coupling power from external power source 35 via external coil 30 and internal coil 65. Headpiece 100 is used to supply power for recharging optional power source 70 with power derived from modulated signal 75. For example, U.S. Pat. No. 4,082,097, which is incorporated herein by reference, discloses a system for charging a rechargeable battery in an implanted human tissue stimulator by means on an external power source.

In addition to transmitting information and data from the external coil to the implanted device, some implantable devices may also transmit information and data back to an external device relating to the status of the device and the signals it senses in the patient's body. Such backtelemetry data may include, e.g., an indication of the voltage level obtained by rectifying and filtering the inductively-coupled carrier signal received from external coil 30. Such voltage will be at a peak (maximum) value when the implant coil 65 and external coil 30 are properly aligned. Thus, such signal may be used as a feedback signal to trigger circuitry within the headpiece whenever proper alignment and/or improper alignment exists. See U.S. Pat. Nos. 5,324,316; 5,312,439; and 5,358,514; which describe a small implantable microstimulator and are incorporated herein by reference. Therefore, while the invention is described herein with the "transmission" coil, or primary coil, in the external portion and the "receiver" coil, or secondary coil, in the implanted portion, it should be understood that for some applications, data (or even power) could be transmitted from the implanted coil to the external coil, as described above.

Figure 1B:
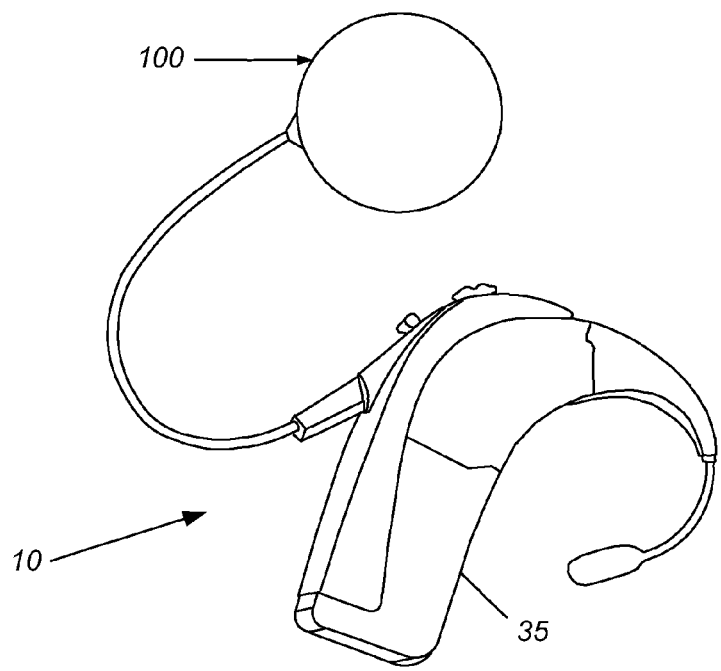
Figure 1E:
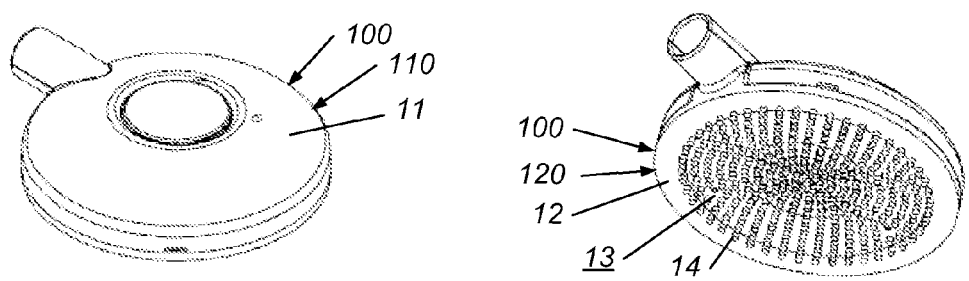
Figure 1E:
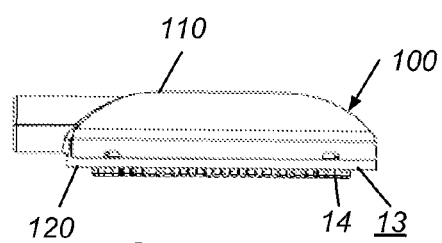

FIGS. 1C-1E show detail of the headpiece 100 of FIG. 1B. FIG. 1C is a top perspective view of headpiece 100 showing a top cover 110 having a top face 11. FIG. 1D is a bottom perspective view of headpiece 100 showing a bottom cover 120 having a bottom (skin-side) face 12 having a surface 13 from which protrude flexible bumps 14. FIG. 1E is a side view of headpiece 100 showing the side of both top cover 110 and bottom cover 120 with flexible bumps 14 protruding from surface 13.

FIGS. 2 and 2A show side views of two embodiments of the headpiece 100 having a top face 11 and a bottom (or skin-side) face 12 having a surface 13 from which protrude flexible bumps 14. FIGS. 3 and 3A are side cross sectional views of the embodiments of headpiece 100 shown in FIGS. 2 and 2A, respectively, showing external coil 30 and external magnet 102. The top cover 110 and bottom cover 120 of the headpiece 100 may comprise, for example, a blend of polycarbonate and acrylonitrile butadiene styrene (ABS). Surface 13 may comprise a rubber or other elastomeric coating, molding, or other covering on bottom cover 120 of headpiece 100. Alternatively, surface 13 may be formed by the housing of headpiece 100, with flexible bumps 14 adhered directly to surface 13 or formed by injecting rubber through holes in the housing to form flexible bumps 14 protruding from surface 13, as will be described in more detail below. Flexible bumps 14 may be molded from the same material as the surrounding surface 13, or may comprise different material. Flexible bumps 14 may comprise, for example, a thermoplastic elastomer (TPE) such as SANTOPRENE TPE or VERSOLLAN TPE, or a silicone rubber such as SILASTIC silicone elastomer. The flexible bumps 14 preferably comprise material having a durometer of between 20 and 70 Shore A, preferably between 30 and 70 Shore A, and more preferably between 30 and 60 Shore A, and most preferably about 50 Shore A.

Figure 27:
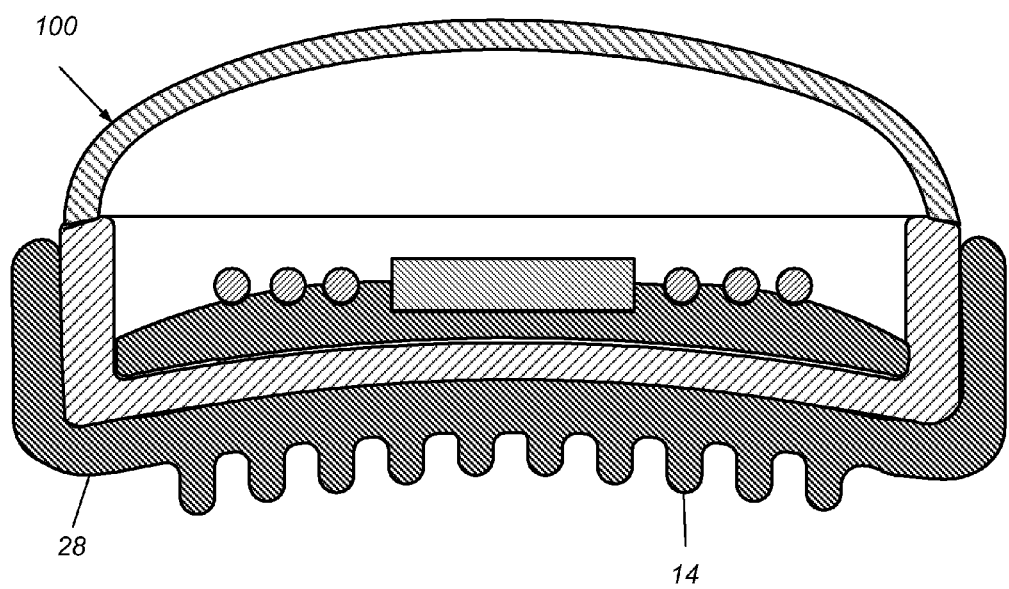
FIG. 27 is a side cross sectional view of another alternative embodiment of the present invention.

While flexible bumps 14 may be permanently attached to headpiece 100, such as by permanently adhering to the bottom of the housing or by being formed integral with a covering that may be molded or bonded or the like to at least the bottom face of the housing of headpiece 100, flexible bumps 14 may alternatively be supplied as part of a removable or detachable pad or envelope. As used herein with respect to the inventive flexible bumps, detachable means designed to be removed from the headpiece without damaging either the headpiece or the detachable piece; removable means designed to be removed from the headpiece without damaging the headpiece. A pad may be adhesively applied to the bottom of headpiece 100; alternatively, the pad may engage with the headpiece 100 using a fastener or one or more engaging features. The pad may form a cap 28 that fits over the bottom of the headpiece 100 and extends partway up the sides, as illustrated in FIG. 27. The amount that it extends is not limited, but greater extension provides for more secure attachment. To install the cap 28, the cap is placed over the bottom of the headpiece 100, and air is then pushed out through a hole in the bottom of the cap (not shown) or burped out from between the cap and headpiece by peeling back an edge of the cap and pressing the cap against the headpiece, creating a suction effect, which helps hold the cap in place. The cap remains in place on the headpiece due to the suction effect and frictional engagement with the headpiece. Alternatively, the headpiece may be placed within an envelope having flexible rubber bumps on at least one surface such that the bumps are facing the skin when the headpiece is in use. The envelope may be similar to the pouch described in U.S. Pat. No. 5,948,006, incorporated herein by reference. The envelope may completely cover the headpiece, and may provide water resistance; alternatively, portions of the headpiece may be exposed instead of covered by the envelope, such as to avoid attenuation in the region of a microphone. A cap or envelope configuration would generally be considered detachable since the headpiece could be removed from the cap or envelope without damaging either the headpiece or cap or envelope. The pad having adhesive may be detachable, but may alternatively be considered removable because, although removing the pad would not damage the headpiece, the adhesive may allow only limited or no reuse of the pad. Having the bumps permanently attached to the headpiece will generally allow for a thinner profile; on the other hand, detachability or removability may be advantageous for cleaning, replacing, or providing different thicknesses, colors, or the like. Providing various pad or envelope thicknesses or different heights of bumps provides adjustability of the attraction force between the implanted and external magnet by varying their distance.

Flexible bumps 14 may be of any shape and size, but are preferably of a size and shape that aids in retaining headpiece 100 against the skin while allowing blood to flow in regions of skin adjacent the bumps. The length of each bump as measured from surrounding surface 13 is preferably between 0.010 and 0.040 inches, and more preferably 0.020 to 0.040 inches. The bumps preferably have a maximum width of between 0.010 and 0.040 inches and more preferably between 0.020 and 0.040 inches, and most preferably between 0.020 and 0.035 inches. For bumps that are circular in cross section, such as those shown in FIGS. 2-8, this width is the diameter. For bumps having other cross-sectional shapes, such as square or rectangular, this width is the largest width dimension. The tips of the bumps may be convex, flat, concave, or any other shape. Bumps with concave tips, such as shown in FIG. 7, may provide additional adhesion to the skin by acting as suction cups.

Figure 26:
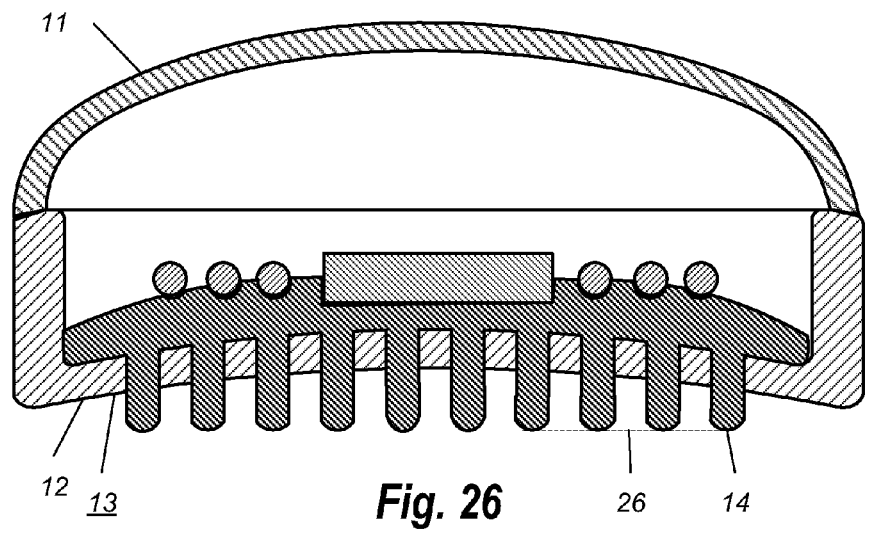
FIG. 26 is a side cross sectional view of another alternative embodiment of the present invention.

The bottom face 12 of the headpiece 100 is preferably generally concave, as illustrated in FIGS. 2, 2A, 3, and 3A, but may be flat or of any shape. The lengths of the bumps may be the same as each other, as in the embodiment shown in FIG. 2A, or may vary, as in the embodiment shown in FIG. 2. For example, the face 12, whether flat or concave, may have longer bumps on one or more outer concentric rings and shorter bumps on inner rings, which may create a similar effect as having the surrounding surface 13 of a concave shape. As another alternative, adjacent bumps can be different sizes, differing in both length and width. Longer bumps may be thinner and shorter bumps fatter, for example. By having different sizes, as the longer bumps deflect, the shorter bumps are recruited to take more of the load. As yet another embodiment, illustrated in FIG. 26, the bottom face 12 may be concave, but the lengths of the bumps may vary such that the bumps at the periphery are shorter and therefore stiffer than the bumps in the center, which are longer and therefore more flexible. As seen in its relaxed condition, the tips of the bumps line up to form a flat surface, as shown by the dashed line 26, even though the bottom face 12 is concave. However, when positioned on the skin, the flexible bumps follow the natural curvature of the head, with those bumps in the center deforming under the load of magnetic attraction because of their relative flexibility. Although the bumps are illustrated in the figures as lying in a direction parallel to the axis of the headpiece, the bumps may alternatively extend perpendicularly from the surface 13 or at any other angle.

FIGS. 4 and 4A show bottom (skin-side) views of the headpiece 100 showing an array of flexible bumps 14. As shown in FIG. 4A, at least some of the bumps may be arranged in one ring or more rings, which may be concentric. However, their arrangement is not limited. It should be understood that any configuration of a plurality of bumps is possible. Advantageously, maximizing the surface area covered by bumps minimizes the pressure against the skin. For example, for a circular headpiece, it may be preferable to have bumps covering a substantial area of the circle instead of just in a ring at the perimeter. Furthermore, the bumps may be substantially uniformly distributed across the circle, or there may be more bumps in the middle or more at the periphery. The key is to minimize pressure against the skin while allowing adequate blood flow.

Figure 5:
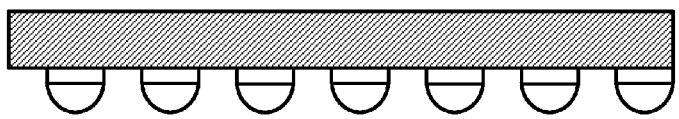
FIGS. 5-11 are cross sectional side views, each with a bottom view of a single bump, of various embodiments of the bottom portion of the present invention.
Figure 6:
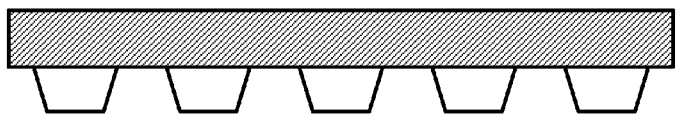
Figure 7:
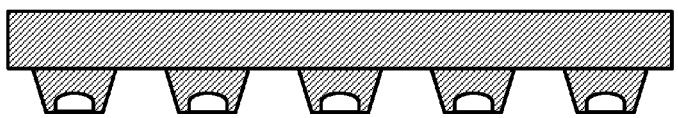
Figure 8:
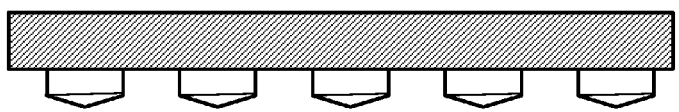
Figure 9:
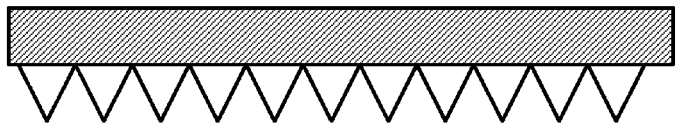
Figure 10:
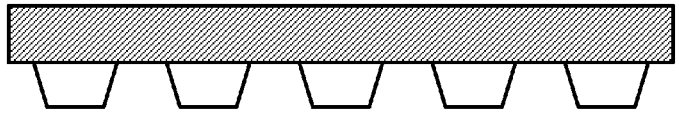
Figure 11:
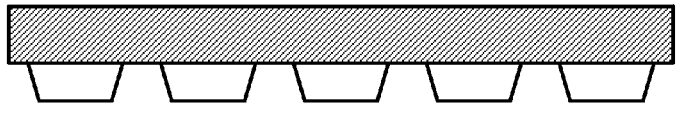

FIGS. 5-11 are cross sectional side views and a bottom view of a single bump of various embodiments of the bottom surface of headpiece 100. These views are meant only as examples; the shape is not limited to these shapes. As used herein, the "base" of the bump is that portion extending from the bottom surface, and the "tip" of the bump is that portion that will contact the skin. FIG. 5 shows bumps having a right cylindrical base and a hemispherical tip, which has the advantage of being one of the easier shapes to manufacture. FIG. 6 shows frustoconical bumps having a conical base and flat tip. FIG. 7 shows bumps having a conical base and concave tip. FIG. 8 shows bumps having a right cylindrical base and a conical tip. FIG. 9 shows bumps having a regular pyramidal base extending to a pointed tip. FIG. 10 shows bumps having a tapered rectangular base that is truncated to form a flat rectangular tip. FIG. 11 shows bumps having a rectangular base tapering to a wedge-shaped tip.

Figure 12:
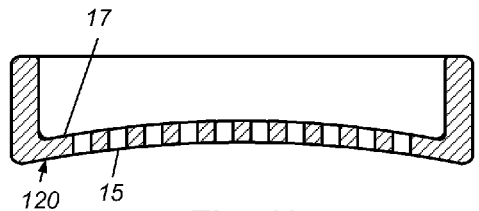
FIGS. 12-15 illustrate steps for manufacturing a headpiece according to one embodiment of the present invention.
Figure 13:
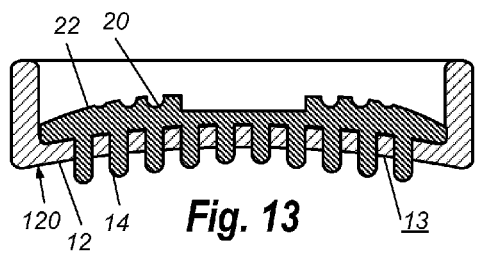
Figure 14:
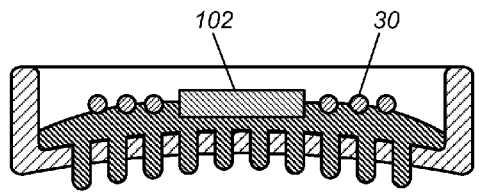
Figure 15:
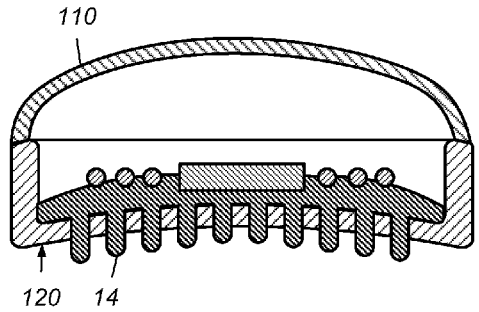

FIGS. 12-15 illustrate steps for manufacturing a headpiece according to one embodiment of the present invention. In FIG. 12, a bottom cover 120 is provided, having an inside face 17, a bottom face 12, and holes 15 therethrough. In FIG. 13, an elastomeric material 22 is added to the bottom cover 120, such as from the inside face 17, flowing through holes 15, and forming flexible bumps 14 protruding from surface 13 of the bottom face 12, and forming magnet and antenna coil locating features 20 on a portion of the elastomeric material inside the bottom cover. The step illustrated in FIG. 13 can be accomplished in a number of ways, such as by insert molding with liquid silicone rubber, transfer molding, or compression molding, or casting. Note that the elastomeric material 22 is continuous from the inside to the outside of the headpiece, forming a strong, permanent mechanical lock of the elastomeric material. In FIG. 14, a magnet 102 and an antenna coil 30 are placed within the bottom cover 120, taking advantage of the locating features 20 formed in the elastomeric material 22. Note that some of the locating features 20 may be formed by the bottom cover 120 itself, as will be illustrated later. In FIG. 15, a top cover 110 is joined to the bottom cover 120, sealing the magnet 102 and coil 30 within the headpiece 100.

Figure 16:
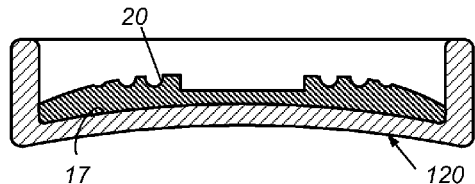
FIGS. 16-19 illustrate steps for manufacturing a headpiece according to an alternative embodiment of the present invention.
Figure 17:
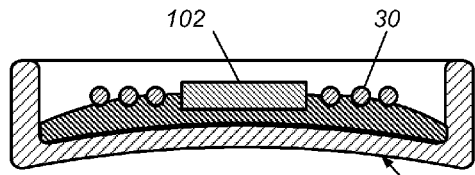
Figure 18:
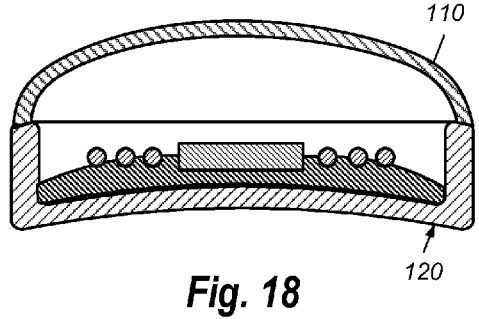
Figure 19:
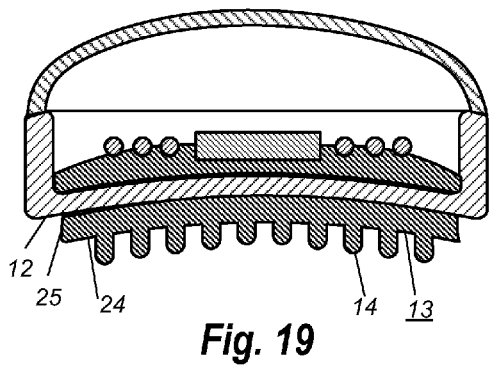

FIGS. 16-19 illustrate steps for manufacturing a headpiece according to an alternative embodiment of the present invention, which may have a detachable or removable pad containing the flexible bumps 14. As shown in FIG. 16, in this embodiment, a bottom cover 120 is provided, but without through holes. The bottom cover 120 has magnet- and coil-locating features 20, which may be molded into the bottom cover material itself or may be added by an elastomeric or other material molded or cast into the bottom cover or provided as a separate part and glued or otherwise attached to the inside surface 17 of the bottom cover. In FIG. 17, the magnet 102 and antenna coil 30 are placed within the bottom cover 120, using the locating features 20. In FIG. 18, a top cover 110 is joined to the bottom cover 120, sealing the magnet 102 and coil 30 within. In FIG. 19, an elastomeric pad 24 having a plurality of flexible bumps 14 is adhered to the bottom face 12 either by molding it directly to the bottom face 12 of the bottom cover 120 or by forming the elastomeric pad with bumps first and then adhering it with an adhesive, engagement features, or other method, to the bottom face 12.

As can be seen by directly comparing FIGS. 15 and 19, the embodiment of FIG. 15 provides an advantage of not requiring the additional thickness of the pad, which could be about 1 mm. It has the added advantage of supporting the flexible bumps 14 with the bottom cover 120, which may be relatively rigid, allowing the bumps to be made of the most flexible material possible. It also provides an advantage of more securely fixing the bumps to the bottom cover 120. For example, the edge 25 of the pad 24 of FIG. 19 might have a tendency to peel off of the bottom face 12 whereas there is no edge in the embodiment of FIG. 15 to peel off. On the other hand, the embodiment of FIG. 19 may be preferred when removability or detachability of bumps is desired, such as to change pad thickness or to another geometry or for cleaning.

Figure 20:
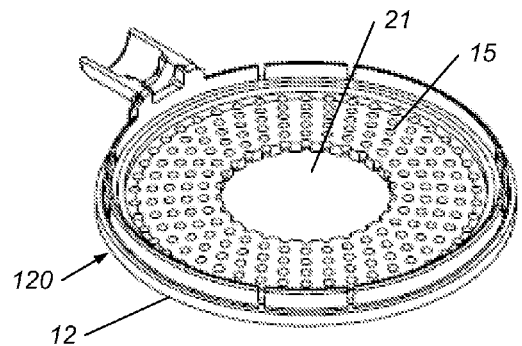
FIG. 20 is a perspective view of the inside bottom cover of the headpiece according to one embodiment of the present invention.

FIG. 20 is a perspective view of the inside of the bottom cover 120 of a headpiece according to one embodiment of the present invention, showing the holes 15. This embodiment has a large open area 21 in the center portion such that surface 13 of the completed headpiece will be formed by the hard plastic bottom cover 120 on the outer portion, and the inner portion will be formed by the molded elastomer. This provides rigidity in the outer region and conformity in the center region.

Figure 21:
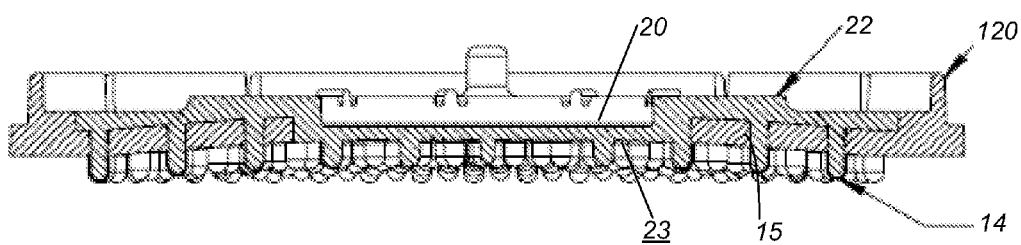
FIG. 21 is a side cross sectional view of the completed bottom portion of the headpiece including the bottom cover shown in FIG. 20.

FIG. 21 is a side cross sectional view of the completed bottom portion of the headpiece, showing flexible bumps 14 extending through holes 15 in the hard bottom cover 120 of FIG. 20, and showing an elastomeric surface 23 formed during the molding process in the center portion. Various features 20 can be seen molded into the hard bottom cover 120 and the elastomer 22 for locating the magnet and antenna coil.

Figure 22:
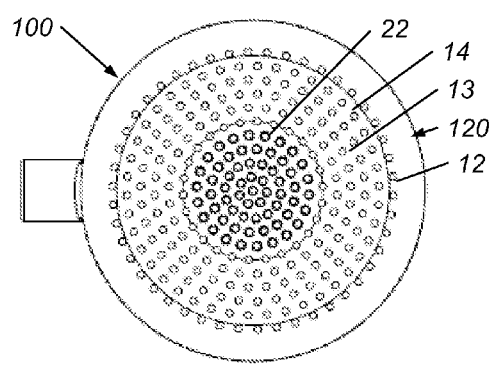
FIG. 22 is a bottom view of the completed headpiece including the bottom portion shown in FIG. 21.

FIG. 22 is a bottom view of the completed headpiece 100 of FIGS. 20 and 21, showing flexible bumps 14 protruding from surface 13 of bottom face 12. Surface 13 is formed by the bottom cover 120 on the periphery and by the elastomer 22 in the center portion.

Figure 23:
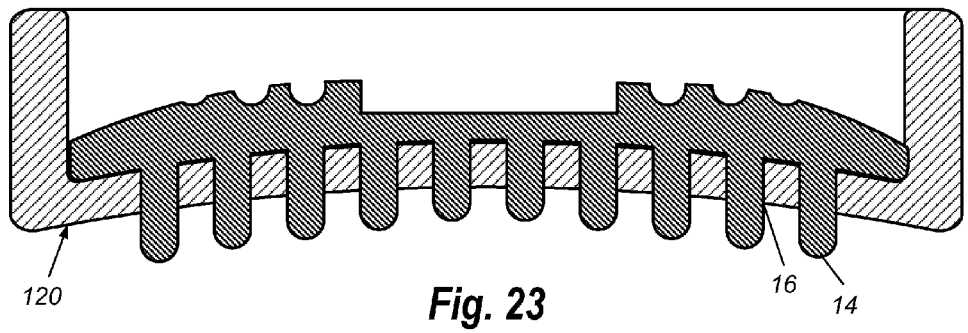
FIG. 23 is a side cross sectional view of a subassembly of one embodiment of the present invention.

FIG. 23 is a side cross sectional view of one embodiment of a portion of the present invention, showing detail of FIG. 13. Since the flexible bumps 14 extend from the hard bottom cover 120 they are more supported and constrained than in the embodiment of FIG. 24, in which a pad 24 is adhered to the bottom cover 120. This provides more positional control of the individual flexible bumps 14, which in turn provides more overall stability to the headpiece.

Figure 24:
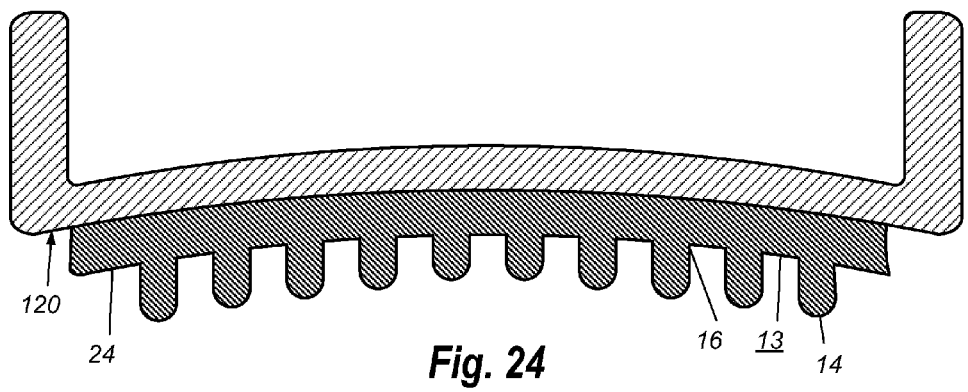
FIG. 24 is a side cross sectional view of a subassembly of an alternative embodiment of the present invention.

FIG. 24 is a side cross sectional view of an alternative embodiment of a portion of the present invention, showing detail of the housing and rubber pad 24 of FIG. 19. Since the rubber pad 24 is flexible, the overall structure will tend to move more than the embodiment of FIG. 23.

Figure 25:
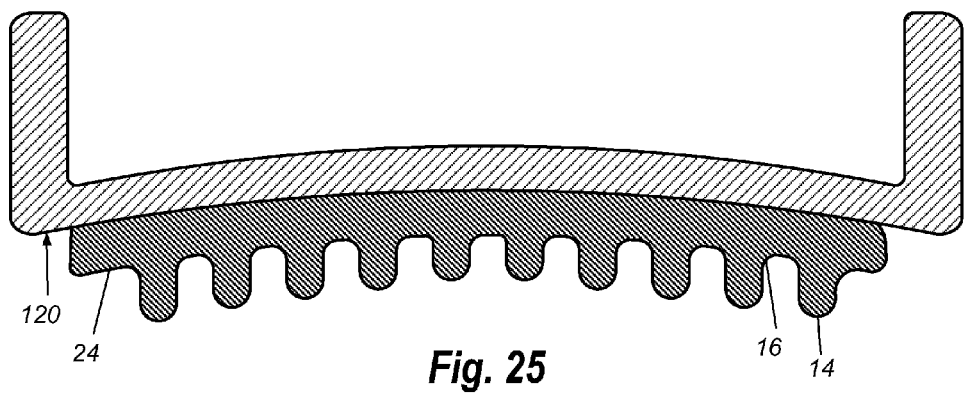
FIG. 25 is a side cross sectional view of a subassembly of another alternative embodiment of the present invention.

FIG. 25 is a side cross sectional view of another alternative embodiment of a portion of the present invention, similar to that shown in FIG. 24, but with fillets formed at the junction 16 of the surface 13 and the flexible bumps 14 to provide support to the flexible bumps 14. This helps maintain positional control of the bumps, providing more overall stability to the headpiece.

From the above, it is thus seen that the present invention provides a device including a transmission coil that is compatible with many types of implanted devices. The headpiece is skin-adhering and coil-aligning via a magnet paired with a magnet of an implanted device, easy to apply and remove, atraumatic, and available in a variety of colors or shapes. The flexible bumps also improve impact resistance, protecting both the headpiece and the underlying implanted coil, by dissipating the energy.

While the invention herein disclosed has been described by means of specific embodiments and applications thereof, numerous modifications and variations could be made thereto by those skilled in the art without departing from the scope of the invention set forth in the claims. For example, invention may take the form of an elastomeric pad having the flexible bumps, wherein the pad comprises a sealed membrane filled with air, liquid, and/or gel to further distribute the forces. While the invention has been described specifically with respect to a "headpiece" for use with a cochlear implant, the headpiece may be for use anywhere on the body aligned with any implanted device, which may comprise a tissue stimulator, sensor, pump, or any other implantable device that requires an electromagnetic link to be established therewith.

What is claimed is:

1. A headpiece, comprising:
   a housing having a bottom surface;
   a transmission coil associated with the housing and coupled to electronic circuitry;
   a magnet associated with the housing that secures the surface of the housing adjacent to skin; and
   an array of flexible bumps associated with and protruding in a direction away from the bottom surface of the housing, the flexible bumps having a base end and a tip end and being arranged such that the tip ends of a first plurality of the flexible bumps together define a concave area and the tips ends of a second plurality of the flexible bumps defines a flat area.

2. The headpiece of claim 1 wherein the bumps comprise elastomeric material.

3. The headpiece of claim 2 wherein the bumps comprise material having a durometer of between 20 and 70 Shore A.

4. The headpiece of claim 3 wherein the bumps comprise material having a durometer of between 30 and 60 Shore A.

5. The headpiece of claim 2 wherein at least some of the bumps are arranged in at least one ring.

6. The headpiece of claim 5 wherein at least some of the bumps are arranged in at least two concentric rings.

7. The headpiece of claim 1 wherein the bottom surface is generally concave and rigid.

8. The headpiece of claim 1 wherein the bottom surface comprises a material different from the material of the bumps.

9. The headpiece of claim 1 wherein the flexible bumps are permanently attached to the headpiece.

10. The headpiece of claim 1 wherein the flat area is located radially inward of the concave area.

11. The headpiece of claim 1 wherein the concave area extends continuously around the flat area.

12. A headpiece, comprising:
    a housing having a bottom surface;
    a transmission coil associated with the housing and coupled to electronic circuitry;
    a magnet associated with the housing that secures the bottom surface of the housing adjacent to skin; and
    an array of flexible bumps, defining base ends and tip ends, associated with and protruding in a direction away from the bottom surface of the housing such that the tips ends are located between 0.010 and 0.040 inches from the bottom surface of the housing.

13. The headpiece of claim 12 wherein the tip ends of the bumps are located between 0.020 and 0.040 inches from the bottom surface of the housing.

14. The headpiece of claim 12 wherein the bottom surface comprises a covering material and wherein said bumps are integral with the covering material.

15. The headpiece of claim 12 wherein the flexible bumps are removably attached to the housing.

16. The headpiece of claim 12 wherein the flexible bumps are detachably attached to the housing.

17. The headpiece of claim 16, further comprising a flexible envelope comprising the flexible bumps.

18. A headpiece, comprising:
    a housing having a bottom surface;
    a transmission coil associated with the housing and coupled to electronic circuitry;
    a magnet associated with the housing that secures the bottom surface of the housing adjacent to skin; and
    an array of flexible bumps associated with and protruding in a direction away from the bottom surface of the housing, the bumps having a maximum width of between 0.010 and 0.040 inches.

19. The headpiece of claim 18 wherein the bumps have a maximum width of between 0.020 and 0.040 inches.

20. The headpiece of claim 18 wherein the bottom surface comprises a covering material and wherein said bumps are integral with the covering material.

21. The headpiece of claim 18 wherein the flexible bumps are removably attached to the housing.

22. The headpiece of claim 18 wherein the flexible bumps are detachably attached to the housing.

23. A rubber pad for use on the skin-side face of a headpiece comprising:
    a disk or ring of rubber having:
    a thickness of less than 0.1 inches; and
    a concave surface having a plurality of flexible bumps protruding about 0.010 to 0.040 inches therefrom, wherein the bumps have a hardness of 20 to 70 Shore A durometer and a width of about 0.010 to 0.040 inches.

24. A medical device system comprising:
    implantable componentry comprising an internal coil, an internal magnet, and internal electronics;
    external componentry comprising an external coil coupled to the internal coil, an external magnet magnetically coupled to the implanted magnet, and external electronics; and
    a headpiece housing the external coil and external magnet and having a plurality of flexible bumps on a rigid concave skin-facing surface thereof.

25. The medical device system of claim 24 wherein the flexible bumps:
    protrude about 0.010 to 0.040 inches from the surface;
    have a width of about 0.010 to 0.040 inches; and
    have a hardness of 30 to 70 Shore A durometer.

* * * * *